United States Patent
Mallough

(10) Patent No.: US 10,940,245 B2
(45) Date of Patent: Mar. 9, 2021

(54) FOOT PEDAL OCCLUSION INDICATOR SYSTEM, APPARATUS, AND METHOD

(71) Applicant: Johnson & Johnson Surgical Vision, Inc., Santa Ana, CA (US)

(72) Inventor: Mitchell W. Mallough, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 79 days.

(21) Appl. No.: 16/240,511

(22) Filed: Jan. 4, 2019

(65) Prior Publication Data

US 2019/0134282 A1 May 9, 2019

Related U.S. Application Data

(62) Division of application No. 14/940,028, filed on Nov. 12, 2015, now Pat. No. 10,195,317.

(51) Int. Cl.
*A61M 1/00* (2006.01)
*A61F 9/007* (2006.01)
(Continued)

(52) U.S. Cl.
CPC .......... *A61M 1/0084* (2013.01); *A61F 9/007* (2013.01); *A61F 9/00745* (2013.01); *A61M 1/0064* (2013.01); *A61M 1/0076* (2013.01); *A61M 3/0233* (2013.01); *G05G 1/506* (2013.01); *G05G 5/03* (2013.01); *H01H 3/14* (2013.01); *A61B 2017/00119* (2013.01);
(Continued)

(58) Field of Classification Search
CPC .............. A61M 1/0084; A61M 1/0064; A61M 1/0076; A61M 3/0233; A61M 2205/18; A61M 2205/3331; A61M 2205/3576; A61M 2205/50; G05G 5/03; G05G 1/506; G05G 1/305; G05G 1/44; H01H 3/14; A61F 9/007; A61F 9/00745; A61B 2017/00119; A61B 2017/00973
See application file for complete search history.

(56) References Cited

U.S. PATENT DOCUMENTS 4,832,685 A 5/1989 Haines
6,674,030 B2 1/2004 Chen et al.
(Continued)

FOREIGN PATENT DOCUMENTS

WO 8607249 A1 12/1986
WO 03088172 A1 10/2003

OTHER PUBLICATIONS

International Search Report and Written Opinion for Application No. PCT/US2016/061521, dated Feb. 1, 2017, 14 pages.

*Primary Examiner* — Amber R Stiles
(74) *Attorney, Agent, or Firm* — Johnson & Johnson Surgical Vision, Inc.

(57) ABSTRACT

A system, method and apparatus for notifying a surgeon of an occlusion in an ocular surgical apparatus are disclosed herein. Through operation of a handpiece of the surgical apparatus, the handpiece may become blocked or occluded. An occlusion detector is configured to sense the occlusion in the handpiece, and an occlusion signal is generated. A control module is provided to send an occlusion warning signal to a foot pedal of the surgical apparatus, where a tactile notification is provided to a user of the apparatus that an occlusion has occurred.

13 Claims, 8 Drawing Sheets

(51) Int. Cl.
  *G05G 5/03*    (2008.04)
  *A61M 3/02*    (2006.01)
  *G05G 1/50*    (2008.04)
  *H01H 3/14*    (2006.01)
  *A61B 17/00*   (2006.01)
  *G05G 1/30*    (2008.04)
  *G05G 1/44*    (2008.04)

(52) U.S. Cl.
  CPC .............. *A61B 2017/00973* (2013.01); *A61M 2205/18* (2013.01); *A61M 2205/3331* (2013.01); *A61M 2205/3576* (2013.01); *A61M 2205/50* (2013.01); *G05G 1/305* (2013.01); *G05G 1/44* (2013.01)

(56) References Cited

U.S. PATENT DOCUMENTS

| | | | |
|---|---|---|---|
| 6,962,581 B2* | 11/2005 | Thoe | A61B 17/00 200/51.02 |
| 7,012,203 B2 | 3/2006 | Hanson et al. | |
| 2002/0198553 A1 | 12/2002 | Schumer et al. | |
| 2003/0051985 A1 | 3/2003 | Chen et al. | |
| 2004/0035242 A1 | 2/2004 | Peterson et al. | |
| 2004/0092921 A1* | 5/2004 | Kadziauskas | B06B 1/023 606/27 |
| 2005/0245910 A1 | 11/2005 | Wright et al. | |
| 2006/0135907 A1 | 6/2006 | Remde et al. | |
| 2007/0249286 A1* | 10/2007 | Ma | H04L 63/08 455/41.3 |
| 2009/0048607 A1 | 2/2009 | Rockley | |
| 2013/0169412 A1 | 7/2013 | Roth | |
| 2014/0036864 A1 | 2/2014 | Arnott et al. | |
| 2015/0051607 A1 | 2/2015 | Hajishah et al. | |

* cited by examiner

FOOT PEDAL OCCLUSION INDICATOR SYSTEM, APPARATUS, AND METHOD

RELATED APPLICATIONS

This application claims priority to and is a divisional of U.S. patent application Ser. No. 14/940,028, filed Nov. 12, 2015, the entire contents of which is incorporated herein by reference in its entirety.

BACKGROUND

Field of Invention

The present disclosure relates generally to medical methods, systems and apparatuses, and more particularly, to methods, systems and apparatus for detecting and indicating one or more surgical aspects of a medical procedure.

Description of Related Art

Ophthalmic surgical apparatuses typically include operating controls for regulating settings or functions of the apparatus. Numerous types of apparatuses include, as part of the apparatus, a hand-held medical implement or tool, such as a handpiece with a tip. Operation of the tool requires control of various operating settings or functions based on the type of tool used and the type of operation being performed. Such apparatuses typically include a control module, power supply, an irrigation source, one or more aspiration pumps, as well as associated electronic hardware for operating a multifunction handheld surgical tool in order to emulsify eye tissue, irrigate the eye with a saline solution, and aspirate the emulsified lens from the eye.

A number of medically recognized techniques are utilized for crystalline lens removal based on a variety of technologies, for example, phacoemulsification or vitrectomy. Phacoemulsification and vitrectomy procedures may require fluid control, namely control over aspiration and irrigation to the ocular region, and employ a handpiece that is typically electrically driven and must be controlled. The handpiece or similar apparatus is especially constructed for breaking apart and removing the natural, crystalline lens of a patient's eye, in preparation for insertion of an artificial lens. A phacoemulsification apparatus may involve a console that contains or holds the control module, power supply, and irrigation source, with the console being movable so that these components can be arranged in a beneficial manner during a procedure, typically just outside of the surgical procedure area. The handpiece is arranged to extend into the surgical procedure area, specifically the ocular region.

It should be appreciated that controlling or changing the functions or operations of the handpiece from the remote console or control module is generally unsatisfactory for the surgeon or operator of the handpiece during a surgical operation. During operation, the surgeon's focus should optimally be on the surgical area, not the remote console. Accordingly, in view of the handheld instrumentation necessary for a phacoemulsification procedure, foot controls are frequently provided in order to control and facilitate use of the handpiece, such as a fluid handpiece during surgery, and control of the handpiece may be provided to the surgeon via a foot pedal. Foot pedals vary in design, but more modern foot pedals include a treadle that can be moved in a fore-and-aft direction (a pitch motion) and in a left-and-right direction (a yaw motion). Hard switches may also be provided, where the switches typically provide a toggle functionality and/or an on-off functionality. Control may be provided for various device components and operations for the phacoemulsification, diathermy or vitrectomy machine through the foot pedal, including control of fluid flow, entry into various modes, electrical parameters, speed parameters (e.g. cut speed), and so forth. Despite the output from such foot pedals in regulating or controlling the apparatus, the pedal, and the entire system, must be user friendly in order to provide a surgeon comfort and reliability in its use so as not to initiate disruption of the surgeon's concentration when performing surgery.

Phacoemulsification includes making a corneal and/or scleral incision and the insertion of a phacoemulsification handpiece that includes a needle or tip that is ultrasonically driven to emulsify, or liquefy, the lens. A phacoemulsification system typically includes a handpiece coupled to an irrigation source and an aspiration pump. In various embodiments, the handpiece includes a distal tip that emits ultrasonic energy to emulsify a crystalline lens within the patient's eye. The handpiece includes an irrigation port proximal to the distal tip and coupled to the irrigation source via an irrigation input line. The handpiece further includes an aspiration port at the distal tip that is coupled to the aspiration pump via an aspiration output line. Concomitantly with the emulsification, fluid from the irrigation source (which may be a bottle or bag of saline solution that is elevated above the field of surgery) is irrigated into the eye via the irrigation line and the irrigation port. This fluid is directed to the crystalline lens in the patient's eye in order to maintain the anterior chamber and capsular bag and replenish the fluid aspirated away with the emulsified crystalline lens material. The irrigation fluid in the patient's eye and the crystalline lens material are aspirated or removed from the eye by the aspiration pump and line via the aspiration port. Additionally, some procedures may include irrigating the eye and aspirating the irrigation fluid without concomitant destruction, alteration or removal of the lens.

Phacoemulsification and vitrectomy procedures typically require precise fluid control, namely control over aspiration and irrigation to the ocular region, and employ a handpiece that is typically controlled electrically in order to, for example, precisely control the flow of fluid through the handpiece and tip. Such control is necessary, for example, to maintain a stable volume of liquid in the anterior chamber of the eye, which may be accomplished by irrigating fluid into the eye at the same rate as fluid and/or lens material is aspirated from the eye. During such operations, however, it is possible for the flow of fluid out of or into the handpiece to be occluded or blocked. Such an occlusion may occur, for example, from particles (e.g. particles from the crystalline lens) blocking a port, lumen or tube associated with the irrigation input line or the aspiration output line. Such blockage can disrupt the flow of fluid into or out of the eye, for example, by creating an imbalance of fluid flow that can result in an increased negative pressure in the eye. Conversely, such a blockage could result in a volumetric fluid flow drop off near the aspiration port. For such surgical procedures, it is necessary for the surgeon or other medical personnel to understand and account for specific aspects of the surgical procedure, such as whether a stable volume of fluid is in the eye or whether an occlusion has occurred, in order to effectively perform the operation.

In prior systems, the occurrence of an occlusion has been communicated to a surgeon or user via either an audio tone or a visual indicator on a display associated with a control module of the surgical apparatus. A computer system associated with the control module may be electronically connected to a sensor that monitors the flow of fluid into and out of the handpiece, or a sensor that otherwise detects changes in the rate of fluid flow into the eye or the pressure of the fluid in the eye, in order to determine if an occlusion has occurred. Such a system may be able to detect small changes in the fluid flow rate that would otherwise go unappreciated (or be mistaken) by a surgeon or other user of the handpiece. A pre-determined amount of flow rate change may be programmed into the system, such that if the flow rate change reaches or surpasses the pre-determined amount, the system will know that an occlusion is occurring or has occurred. Other forms of detecting the occurrence of an occlusion are known in the art.

Once an occlusion has been detected, the system will typically sound an audio alarm or provide a visual indicator on the display screen to inform the surgeon of the occlusion. However, such systems have various disadvantages. For instance, use of an audio tone can be distracting or startling to a surgeon or user of the handpiece, who are required to perform detailed and specific movements of the handpiece during a surgical operation. An audio tone may also be startling or intimating for the patient undergoing the surgical procedure. While a traditional audible tone may be enabled or disabled and the volume adjusted, the nature of how occlusions occur, and clear, sometimes results in the rapid cycling of the audible tone (as multiple occlusions occur and clear in quick succession, for example). Such an audible tone may be so distracting that a surgeon prefers to turn the tone off completely.

Alternatively, use of a visual indicator on a display may also be problematic because such visual indicator is displayed on the console of the surgical apparatus. A surgeon is not typically looking at, or even using, a console display while performing surgery, instead keeping the focus of their attention on the patient and the procedure being performed with the handpiece. In illustrative examples, a surgeon may actually be viewing the patient's eye through a surgical microscope and has no view of the console display. One alternative to this is to increase the visual effect of the indicator (larger, brighter, etc.), however if a visual indicator is substantial enough, it can also have the effect of distracting or startling the surgeon and/or patient, as discussed above.

Based on the foregoing, it would be advantageous to provide a means of notification of automatic detection of an occlusion to a surgeon without interruption or distraction to the surgeon or patient during surgery. Such a design would afford a surgeon the ability to perform desired phacoemulsification, diathermy, or vitrectomy functions with less need to worry about an abrupt audio tone, or a potentially unnoticed or distracting visual indicator, when an occlusion is occurring or has occurred. Moreover, such a design would reduce the introduction of human error that can occur during the surgical procedure that occurs because the surgeon is startled by, or does not understand the reason for, the audio or visual signal.

SUMMARY

According to one aspect of the present invention, an ocular surgical apparatus comprises an intraocular lens removal device having a handpiece and a foot pedal for a surgeon to operatively control the surgical device, the handpiece configured to irrigate fluid into the eye and aspirate fluid out of the eye so as to maintain a substantially steady or constant amount of fluid within the eye during surgery, the device further comprising a subsystem or electronic system of the apparatus that detects the occurrence of an occlusion or blockage of fluid flowing into or out of the eye and thereafter causes a vibration mechanism in the foot pedal to vibrate, or a forced feedback mechanism in the foot pedal to increase resistance against compression of the foot pedal, in order to inform the surgeon operating the apparatus about the occlusion.

According to another aspect of the present invention, a method of indicating that an occlusion has occurred in a handpiece of a phacoemulsification/diathermy/vitrectomy system comprises starting a flow of fluid through a tip of the handpiece, sensing whether an occlusion has occurred within the tip, and if an occlusion has occurred, sending an alert or notification signal to a vibration or forced feedback mechanism in a foot pedal of the phacoemulsification/diathermy/vitrectomy system to cause a vibration or forced feedback sensation to be felt by the surgeon's foot.

According to another aspect of the present invention, a vibration mechanism may be located within a foot pedal of a surgical apparatus system, the vibration mechanism configured to receive a command from a control module of the system when the system has detected that an occlusion has occurred in a handpiece being used in the surgical procedure, the vibration mechanism configured to vibrate a treadle, heel cup, or other engaging surface of the foot pedal upon receive of such command, where such engaging surfaces are configured to typically be in contact with the surgeon's foot during the surgical procedure.

According to another aspect of the present invention, a forced feedback mechanism may be located within a foot pedal of a surgical apparatus system, the forced feedback system configured to receive an occlusion alert command from a control module of the system when the system has detected that an occlusion has occurred in a handpiece being used in the surgical procedure, the forced feedback system typically configured to apply a resistance pressure to the treadle of the foot pedal when in use to bias the foot pedal to a unengaged/uncompressed position but permitting downward pitching motion of the treadle when a user applies downward pressure to the treadle, wherein the forced feedback mechanism is further configured to increase the resistance pressure applied to the treadle upon receipt of the occlusion alert command, thereby increasing the amount of pressure a user must apply to the treadle to press down on the treadle during the surgical operation.

Other systems, methods, features and advantages of the invention will be or will become apparent to one of skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The organization and manner of the structure and function of the disclosure, together with the further objects and advantages thereof, may be understood by reference to the following description taken in connection with the accompanying drawings, and in which.

DETAILED DESCRIPTION

The following description and the drawings illustrate specific embodiments sufficiently to enable those skilled in the art to practice the described system and method. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

A system and method for indicating an occlusion has occurred in a tip of a handpiece of a surgical system, which can be applied to any system, medical or non-medical, are disclosed herein. In illustrative embodiments, the system and method include means for automatically detecting the occlusion in the handpiece and automatically sending a signal to a tactile indicator within a foot pedal of the system to cause a tactile notification of the occlusion to be felt by the surgeon using the foot pedal.

Embodiments of a subsystem and method will be discussed herein with a particular emphasis on a medical or hospital environment where a surgeon or health care practitioner performs. For example, an illustrative embodiment of the system is a phacoemulsification surgical system that comprises an integrated high-speed control module for a vitrectomy handpiece that irrigates and aspirates fluid from the eye through a tip connected to the handpiece. The system further comprises sensors to detect whether an occlusion has occurred, such as a sensor that detects whether the flow of fluid into or out of the eye has been disrupted or blocked, and a processor that determines if an occlusion has occurred in the tip of the handpiece from the data collected. The system further includes a foot pedal that used by the surgeon for controlling the handpiece during a surgical operation, the foot pedal further including a tactile indicator that can provide a sensory stimulation to the surgeon's foot when it receives the signal from the processor indicating that an occlusion has occurred.

Figure 1:
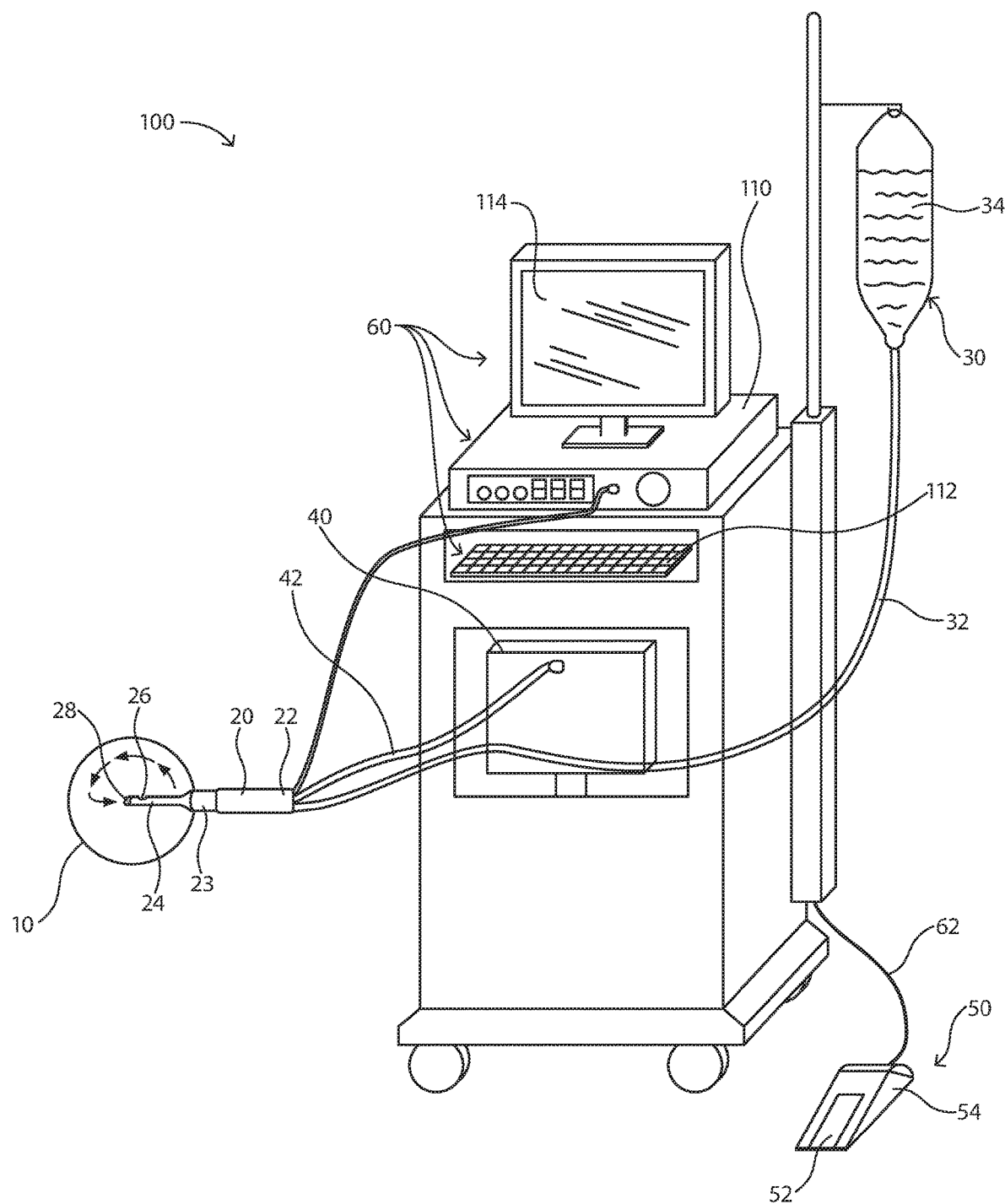
FIG. 1 illustrates a diagram of an exemplary phacoemulsification/diathermy/vitrectomy system in accordance with the present disclosures, the system including a handpiece for use during a surgical procedure and a foot pedal.

FIG. 1 illustrates an exemplary phacoemulsification/diathermy/vitrectomy system 100. As illustrated, the system 100 includes, for example, a handpiece or wand 20, an irrigation source 30, an aspiration source 40, a foot pedal 50, and a control module 60. In this embodiment, fluid is controllably directed through the system 100 in order to irrigate a patient's eye, illustrated representatively at 10, during an ocular surgical procedure. Various embodiments of the handpiece 20, irrigation source 30, aspiration source 40, foot pedal 50, and control module 60 are well known in the art and are embodied in this disclosure.

As illustrated in FIG. 1, the irrigation source 30 is configured to supply a predetermined amount of fluid to the handpiece 20 for use during surgical operation. Specifically, fluid may flow from the irrigation source 30 to the handpiece 20 via an irrigation line 32. The irrigation source 30 may be any type of irrigation source 30 that can create and control a constant fluid flow. For instance, the irrigation source 30 may create and control a constant fluid flow such that vacuum pressure may be determined in the fluid flow, as known in the art. In illustrative embodiments, the irrigation source 30 may be configured to be an elevated drip bag 34 that supplies a steady state of fluid to the irrigation line 32. In illustrative embodiments, a pressure supply (not shown) may be coupled to the irrigation source 30 in order to maintain a constant pressure in the irrigation source 30 as fluid exits the irrigation source 30, as is known in the industry. Other embodiments of a uniform irrigation source are well known in the art.

During the surgical procedure, fluid may be delivered to the eye via the handpiece 20, and fluid may further be aspirated from the eye via the handpiece 20 to flow through an aspiration line 42 to the aspiration source 40. The aspiration source 40 may be any type of aspiration source 40 that aspirates fluid and material from the eye. For instance, the aspiration source may create a fluid flow such that vacuum pressure may be determined in the fluid flow. In illustrative embodiments, the aspiration source 40 may be configured to be a flow-based pump (such as a peristaltic pump) or a vacuum-based pump (such as a Venturi pump) that are well known in the art. The aspiration source 40 may create a vacuum system to pump fluid and/or material out of the eye via the aspiration line 42.

The handpiece 20 includes a first end 22 and a second end 23 that includes a tip 24. The tip 24 includes an irrigation port 26 and an aspiration port 28. The irrigation port 26 is fluidly coupled to the irrigation line 32 to receive fluid flow from the irrigation source 30, and the aspiration port 28 is fluidly coupled to the aspiration line 42 to receive fluid and/or material flow from the eye. The handpiece 20 and the tip 24 may further emit ultrasonic energy into the patient's eye, for instance, to emulsify or break apart the crystalline lens within the patient's eye. Such emulsification may be accomplished by any known methods in the industry, such as, for example, a vibrating unit (not shown) that is configured to ultrasonically vibrate and/or cut the lens, as is known in the art. Other forms of emulsification, such as a laser, are well known in the art. Concomitantly with the emulsification, fluid from the irrigation source 30 is irrigated into the eye via the irrigation line 32 and the irrigation port 26. During and after such emulsification, the irrigation fluid and emulsified crystalline lens material are aspirated from the eye by the aspiration source 40 via the aspiration port 28 and the aspiration line 42. Other medical techniques for removing crystalline lenses also typically include irrigating the eye and aspirating lens parts and other liquids. Additionally, other procedures may include irrigating the eye and aspirating the irrigating fluid without concomitant destruction, alternation or removal of the lens.

Due to the nature of the tip 24 and the procedures that occur during a surgical operation, the irrigation port 26 and the aspiration port 28 may be aligned close to each other adjacent a distal end of the tip 24. During aspiration from the eye, fluid and/or lens material is circulated through the eye and the aspiration port 28 is configured to remove (for example, by force of suction) the fluid and/or material from the eye. Depending on the size of the lens material and the sizes/types of the irrigation port 26 and the aspiration port 28, lens material may clog or block flow of the irrigation port 26 or the aspiration port 28, known as an occlusion. An occlusion is caused by particles blocking a lumen or tube being used to aspirate or irrigate the eye (e.g. the irrigation port 26 or aspiration port 28). This blockage results in increased vacuum (i.e. increasingly negative pressure) in the aspiration line 42. The longer the occlusion is in place, the greater the vacuum. Once the occlusion is cleared, a resulting rush of fluid from the anterior chamber into the aspiration line 42 can outpace the flow of new fluid into the eye from the irrigation source 30.

The system 100 may be configured to detect such an occlusion occurring at the handpiece during operation, which may be communicated to an operator to permit correction of the occlusion, or permit the operator to adjust the settings of the apparatus accordingly. For instance, the system 100 may include a subsystem (not shown) that detects such an occlusion, as explained, for example, in U.S. Published Application No. 2009/0048607, filed Aug. 13, 2007 and incorporated by reference herein. Other methods for detecting the occurrence of an occlusion are known in the art. The subsystem may communicate to the control module 60 that an occlusion has occurred, and the control module 60 may conduct further analysis or provide a warning indicator to the surgeon that an occlusion has occurred.

As illustrated in FIGS. 2A-6B, the present disclosure is directed to an apparatus and method of communicating the occurrence of an occlusion to a surgeon or operator of the handpiece through use of the foot pedal 50. Specifically, the foot pedal 50 is coupled to the control module 60 via a communication path 62 and includes an occlusion alarm 80. In addition to permitting the operator to control the operation and function of the handpiece 20 via engagement with the foot pedal 50, the communication path 62 also permits the control module 60 to send a signal to the foot pedal 50 to control operation of the occlusion alarm 80. The control module 60 may send a signal to cause the occlusion alarm to engage and alert the operator of an occlusion if an occlusion is detected by the control module 60. The communication path 62 may comprise an electrical wire, as illustrated in FIG. 1, or may be a wireless connection between the control module 60 and the foot pedal 50. Other forms of communication paths 62 are known in the art and encompassed in the present disclosure.

Figure 2A:
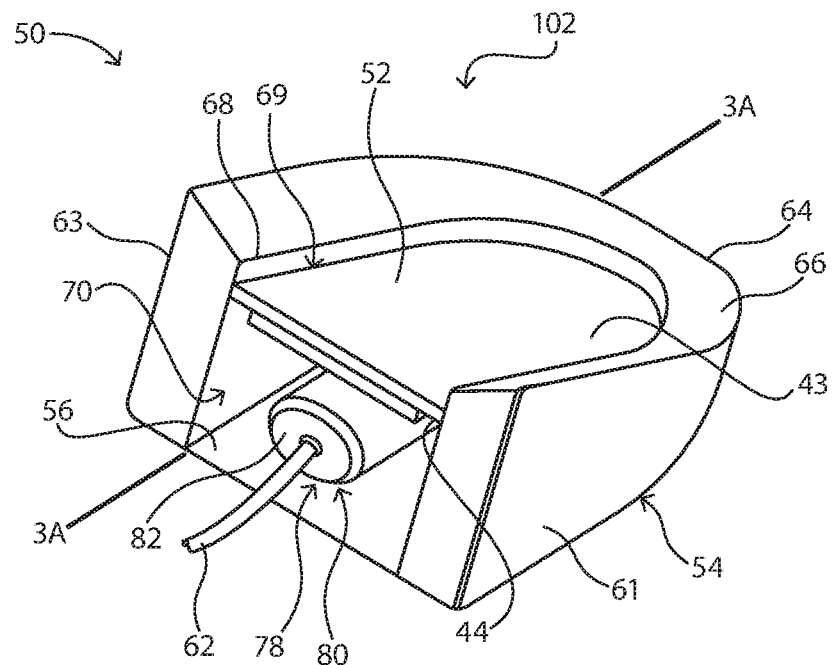
FIG. 2A is a perspective view an exemplary embodiment of a foot pedal in accordance with the present disclosure, the foot pedal in a first uncompressed state.

In illustrative embodiments, the foot pedal 50 comprises a treadle 52, a body housing 54, and a base 56 on which the body housing 54 is mounted, as illustrated for example in FIG. 2A. The base 56 has a bottom surface 58 arranged to lie flat on the ground surface. More specifically, the bottom surface 58 is either flat or a series of separate feet (not shown) may be provided to create a stable base surface on the ground. The base 56 may provide improved stability in various embodiments, including a gripping surface, such as rubber, rubberized, plastic or the like traction strips or treads (not shown).

Figure 2B:
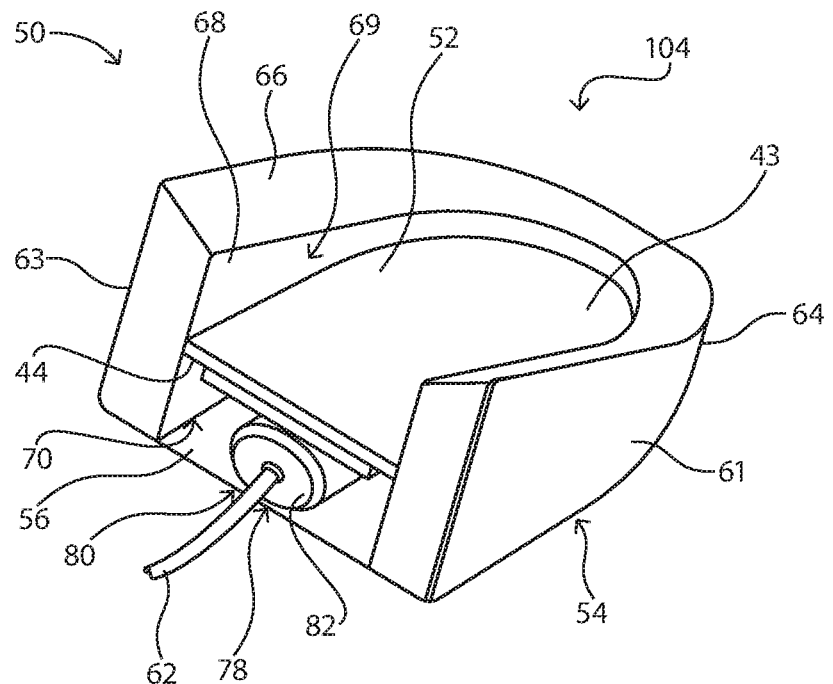
FIG. 2B is a view of the foot pedal of FIG. 2A in a second compressed state.

In illustrative embodiments, the treadle 52 comprises a top surface 43 and a bottom surface 44. The top surface 43 may include traction strips, plastic or rubber surface to provide traction for a user's foot when engaging with the treadle 52. The treadle 52 may be coupled to the body housing 54 to permit rotation of the treadle 52 with respect to the housing 54 about a pivot point 46, as illustrated, for example, in FIGS. 3A and 4A. The treadle 52 may rotate from a first (uncompressed) position 102 to a second (compressed) position 104, and any position therebetween, as illustrated in FIGS. 2A and 2B. In various embodiments, the treadle 52 may be naturally biased to the first position 102 by any known biasing means 48. Such a biasing means may include, for example, a spring 49, but other means of biasing are well known in the art.

In illustrative embodiments, the body housing 54 is configured to extend upward from the base and substantially defines the outer periphery of the foot pedal 50. The body housing 54 comprises a left side wall 61, a right side wall 63, a back side wall 64, and a top surface 66, as illustrated in FIG. 2A. The top surface 66 is configured to include an inner radial edge 68 that defines an aperture 69 into the body housing 54, the aperture 69 configured to receive the treadle 52 as illustrated. The body housing 54 and the base 56 are configured to define an opening 70 within the foot pedal 50 to permit downward rotation of the treadle 52 when the treadle 52 is compressed by a user's foot. In various embodiments, the body housing 54 may further include a front side wall (not shown) connected to the left side wall 61 and the right side wall 63 to further enclose the opening 70.

Figure 4A:
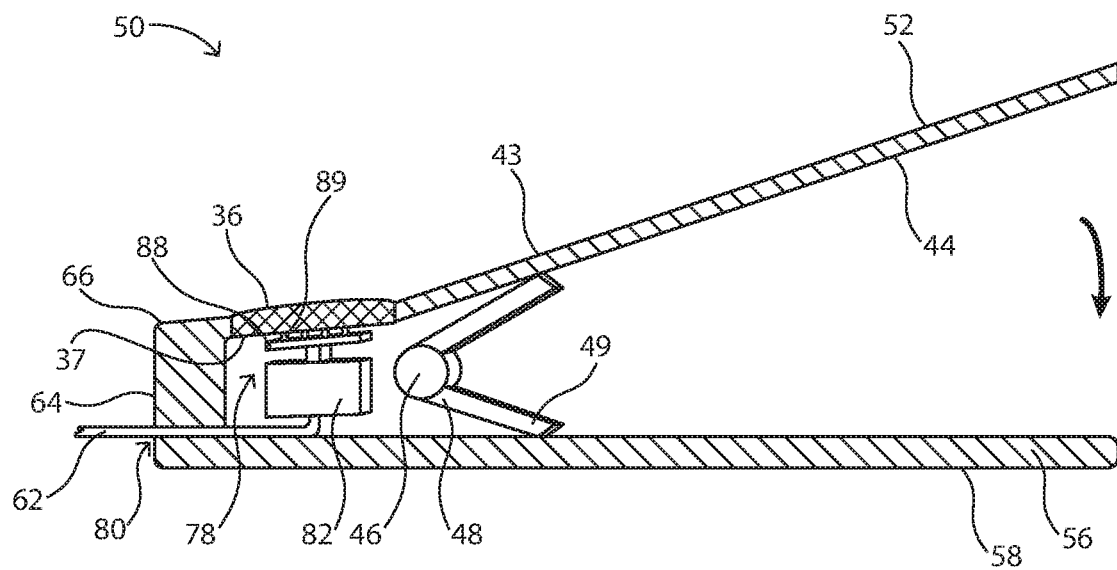
FIG. 4A is a cross-sectional view of another exemplary embodiment of a foot pedal in accordance with the present disclosure.
Figure 4B:
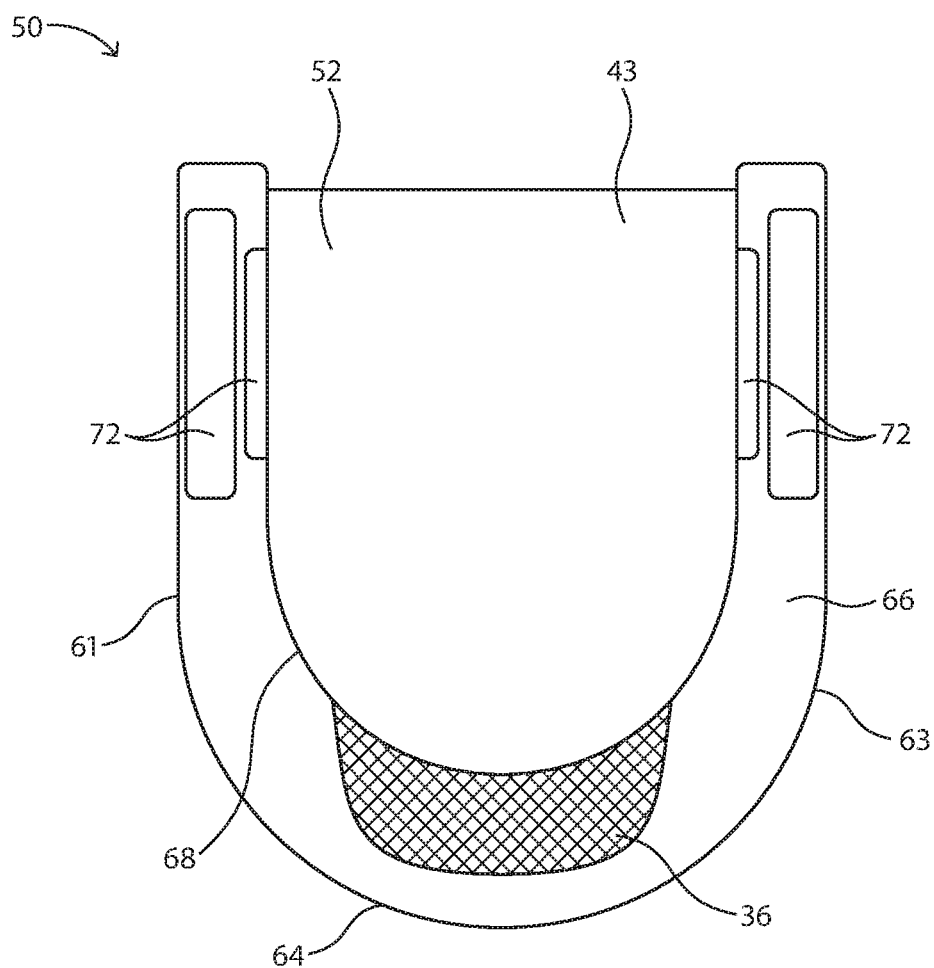
FIG. 4B is a top perspective view of the foot pedal of FIG. 4A.
Figure 5A:
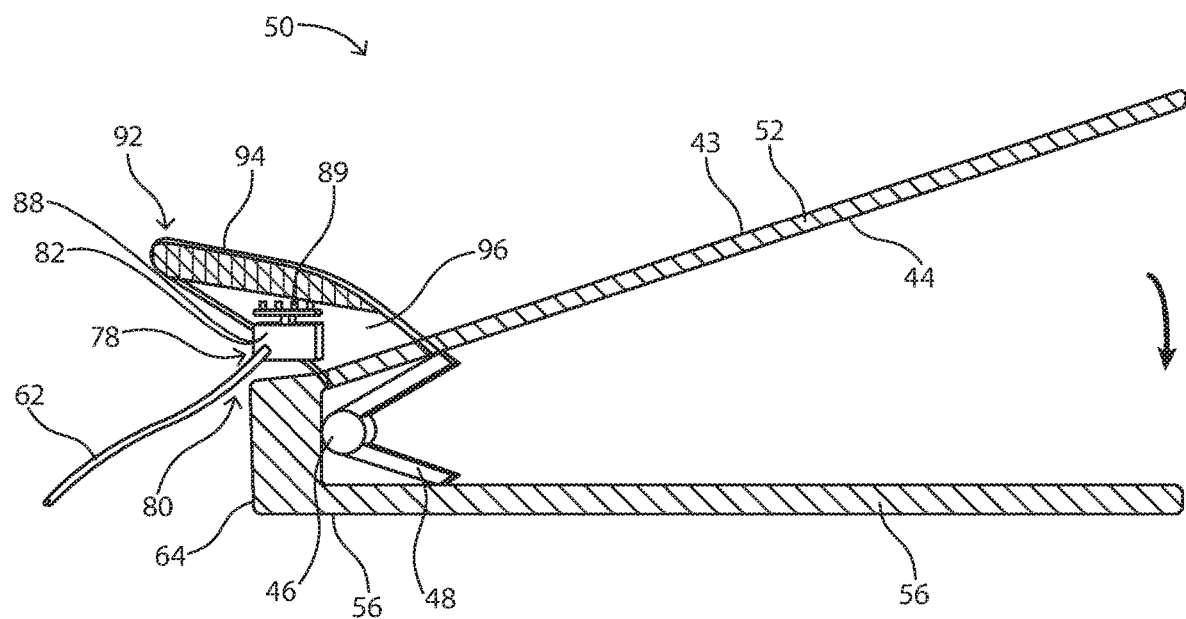
FIG. 5A is a cross-sectional view of another exemplary embodiment of a foot pedal in accordance with the present disclosure.
Figure 5B:
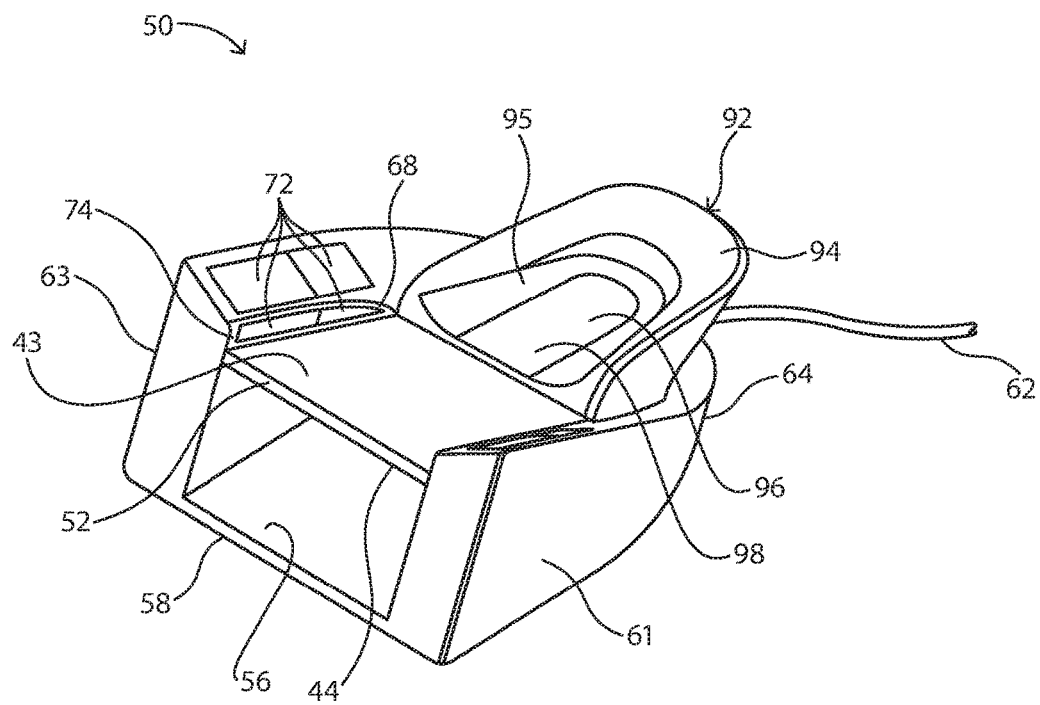
FIG. 5B is a perspective view of the foot pedal of FIG. 5A.

As illustrated in FIG. 4B, the top surface 66 of the body housing may further include one or more switches 72 that may be depressed by a user's foot to engage various functions or operations of the system. Such switches are known in the art, as illustrated, for example, in U.S. Published Application No. 2014/036864, incorporated by reference herein. In other illustrative embodiments, the body housing 54 may also include an inner wall 74 that extends to the inner radial edge 68, the inner wall 74 including further switches 72 for controlling the function of the system, as illustrated in FIG. 5B. Other various configurations of controllers on a foot pedal 50 may include, for example, switches on the treadle. In illustrative embodiments, the switches 72 permit the surgeon to control various functions of the system through communication with the control module 60. In various embodiments, the switches 72 can communicate with the control module 60 via the same communication path 62 that the control module 60 uses to communicate with the occlusion alarm 80.

Figure 3A:
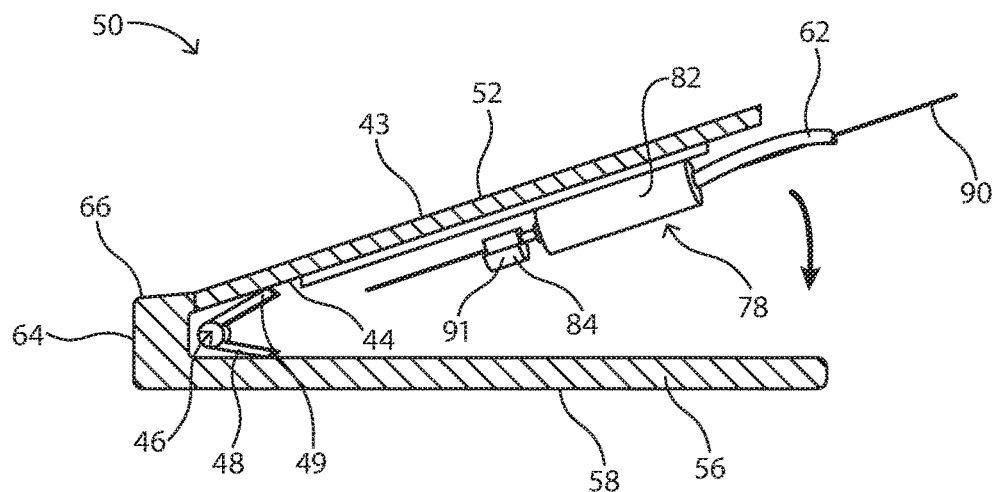
FIG. 3A is a cross-sectional view taken along the line 3A-3A in FIG. 2A.
Figure 3B:
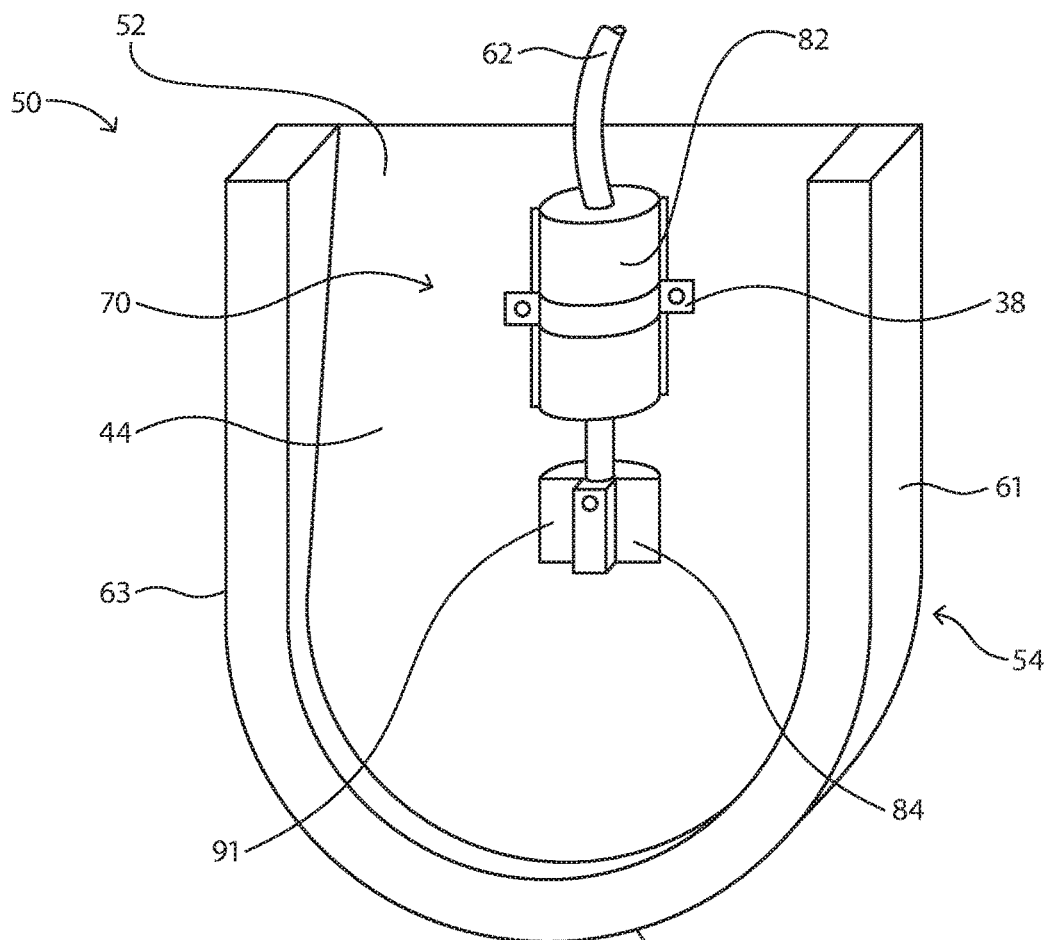
FIG. 3B is a bottom perspective view of a foot pedal in accordance with the present disclosure with a base of the foot pedal removed.

In illustrative embodiments, the occlusion alarm 80 may be a tactile indicator comprising a vibration mechanism 78. The vibration mechanism 78 may include a motor 82 and an off-center weight 84, as illustrated in FIG. 3A. The motor 82 is configured to be electronically coupled to the communication path 62 to receive a signal from the control module 60 when an occlusion has occurred. The motor 82 is configured to rotate the off-center weight 84 upon receipt of the signal that an occlusion has occurred. In illustrative embodiments, the off-center weight may be configured to rotate about a rotation axis 90. In illustrative embodiments, the off-center weight 84 includes a heavier-side portion 91 that rotates about the rotation axis 90 to cause the weight 84 (and components connected to the weight 84) to vibrate. Specifically, when the off-center weight 84 rotates, the imbalance of the heavier-side portion 91 causes the off-center weight and components surrounding the off-center weight to move slightly as the center of gravity shifts. The vibration may occur for as long as the occlusion is detected by the system. Such vibration mechanisms 78 are known, for example, in the electronics industry.

The vibration mechanism 78 may be coupled to various components of the foot pedal 50 to cause the foot pedal 50 to vibrate. For instance, the vibration mechanism 78 may be coupled to the bottom surface 44 of the treadle 52, as illustrated in FIG. 2A. In such an embodiment, the vibration mechanism 78 may be configured to rotate with the treadle 52 about pivot point 46 when the treadle 52 is compressed into the opening 70. The vibration mechanism 78 may be fixedly connected to the bottom surface 44 of the treadle 52, for example via a bracket 38 surrounding the motor 82. In other embodiments, the vibration mechanism 78 may be coupled to the base 56 of the foot pedal 50 and remain stationary when the treadle 52 is compressed. Other connection locations for the vibration mechanism 78 are also within the scope of this disclosure.

In another illustrative embodiment, the vibration mechanism 78 may be configured to cause a heel portion 36 of the top surface 66 of the housing 54 to vibrate. As illustrated in FIGS. 4A and 4B, the heel portion 36 may be located adjacent where an operator's heel would be placed when using the foot pedal 50. The vibration mechanism 78 may be located adjacent the heel portion 36 and configured to vibrate the heel portion 36 when the vibration mechanism 78 is engaged. The vibration mechanism 78 may be of the type as described previously with a motor 82 and an off-center weight 84. Alternatively, the vibration mechanism 78 may include a motor 82 and a rotating vane wheel 88 with one or more projections or fins 89. The rotating vane wheel 88 may be rotated by the motor 82 about a rotation axis 90 to cause the one or more fins 89 to engage with or hit against a bottom surface 37 of the heel portion 36 upon rotation, causing vibrations to the heel portion 36. Other means for causing vibration that can provide tactile notification to an operator are within the scope of this disclosure.

In another illustrative embodiment, the vibration mechanism 78 may be configured within a heel cup assembly 92 connected to the foot pedal 50. As illustrated in FIGS. 5A and 5B, heel portion 36 of the heel cup assembly 92 may include an upper portion comprising a heel loop 94, and a lower portion comprising a heel cup 96. The heel loop 94 may be substantially rigid and may or may not be static during use of the foot pedal 50. Further, the heel loop 94 may be adjustable, such as by allowing for an increase or decrease in the lateral distance from the rearmost point of the heel loop 94 and front most portion of the foot pedal 50. The heel cup 96 may provide at least one angular surface 95 to contact at least a portion of the user's heel to cause the user's heel to be retained or positioned within the cup 96. The heel cup 96 includes a contact surface 98 onto which the heel of the user may rest. When the vibration mechanism 78 is located adjacent the contact surface 98, the contact surface may provide vibration or tactile notification to the user's heel within the heel cup assembly 92 than an occlusion has occurred.

Figure 6A:
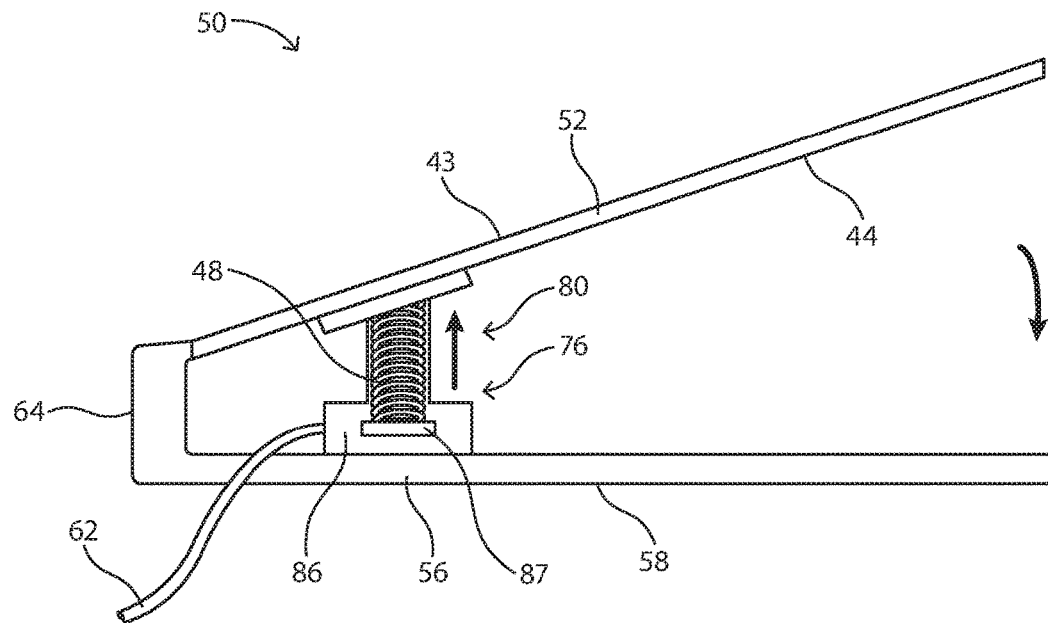
FIG. 6A is a cross-sectional view of another exemplary embodiment of a foot pedal in accordance with the present disclosure.
Figure 6B:
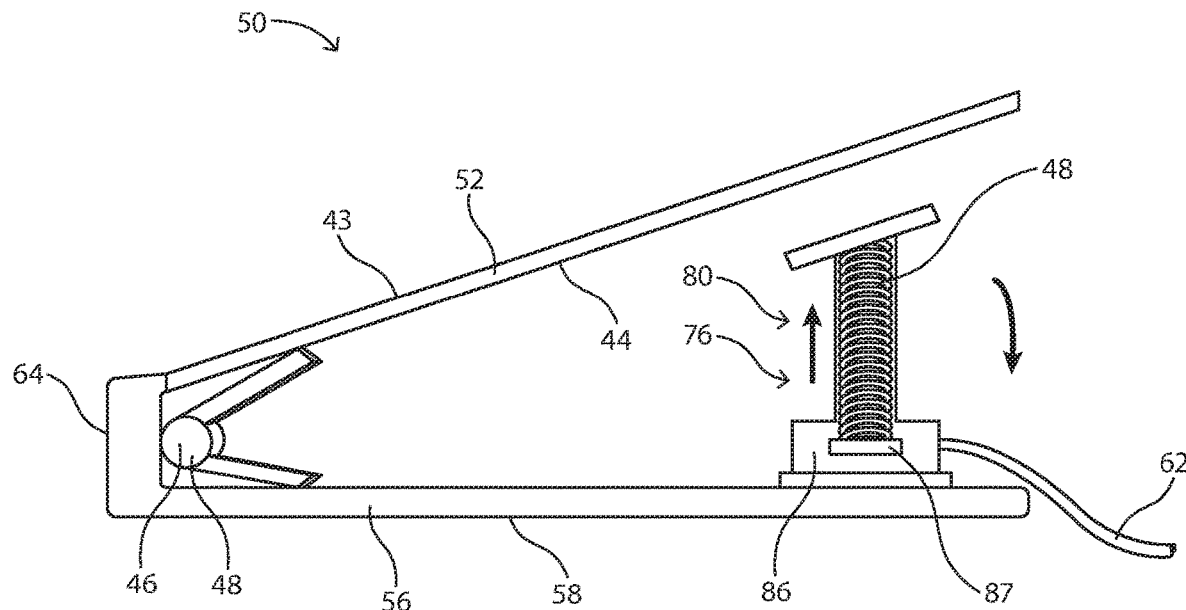
FIG. 6B is a cross-sectional view of another exemplary embodiment of a foot pedal in accordance with the present disclosure.

In another illustrative embodiment, the occlusion alarm 80 may be a tactile feedback indicator comprising a feedback mechanism 76, as illustrated in FIGS. 6A and 6B. The feedback mechanism 76 may include a base 86 coupled to the base 56 of the foot pedal 50. When the control module 60 sends a signal to the base 86 that an occlusion has occurred, the feedback mechanism 76 is configured to create additional upward force or pressure upon the treadle 52. As a user or surgeon presses down on the treadle 52 during operation, the additional upward force or pressure will provide tactile indication that an occlusion has occurred. The additional or increased pressure may remain constant (or increase) until the occlusion has been removed or reduced.

In illustrative embodiments, the upward pressure of the feedback mechanism 76 may be created by a biasing member 48 that is configured to bias against the bottom surface 44 of the treadle 52. The base 86 may include a compression plate 87 or other similar device that can provide compressive force against the biasing member 48. The feedback mechanism 76 may be positioned anywhere along the length of the base 56 of the foot pedal 50 (as illustrated for example in FIGS. 6A and 6B) such that it can engage with the bottom surface 44 of the treadle 52. Other embodiments for a force feedback are envisioned, e.g. force applied to or adjustment to the tension of biasing means 48.

Figure 7:
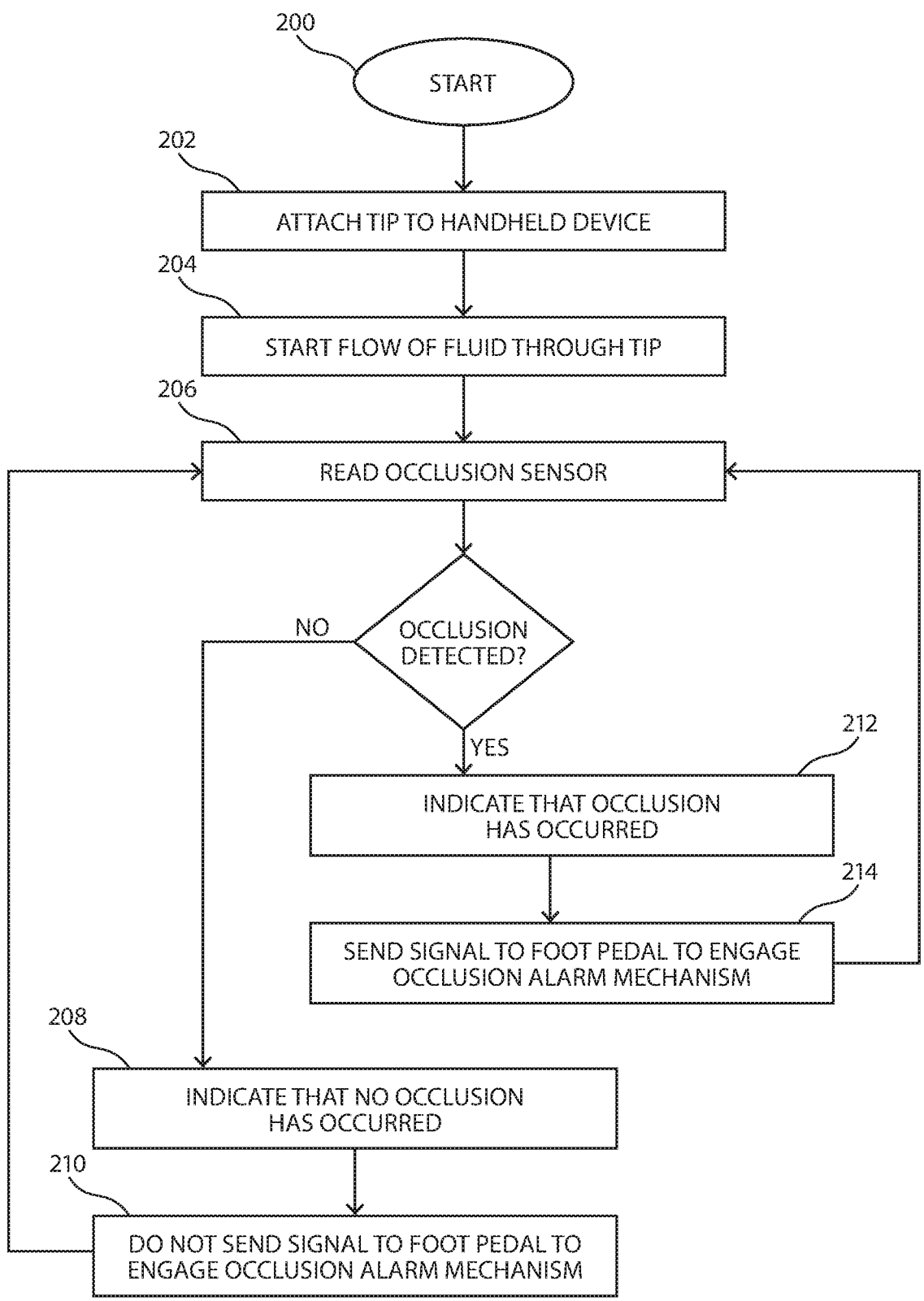
FIGS. 7 and 8 illustrate block diagrams showing a flow chart an embodiment of the method of the utilizing the system of FIG. 1 in accordance with the present disclosure to perform a surgical procedure.
Figure 8:
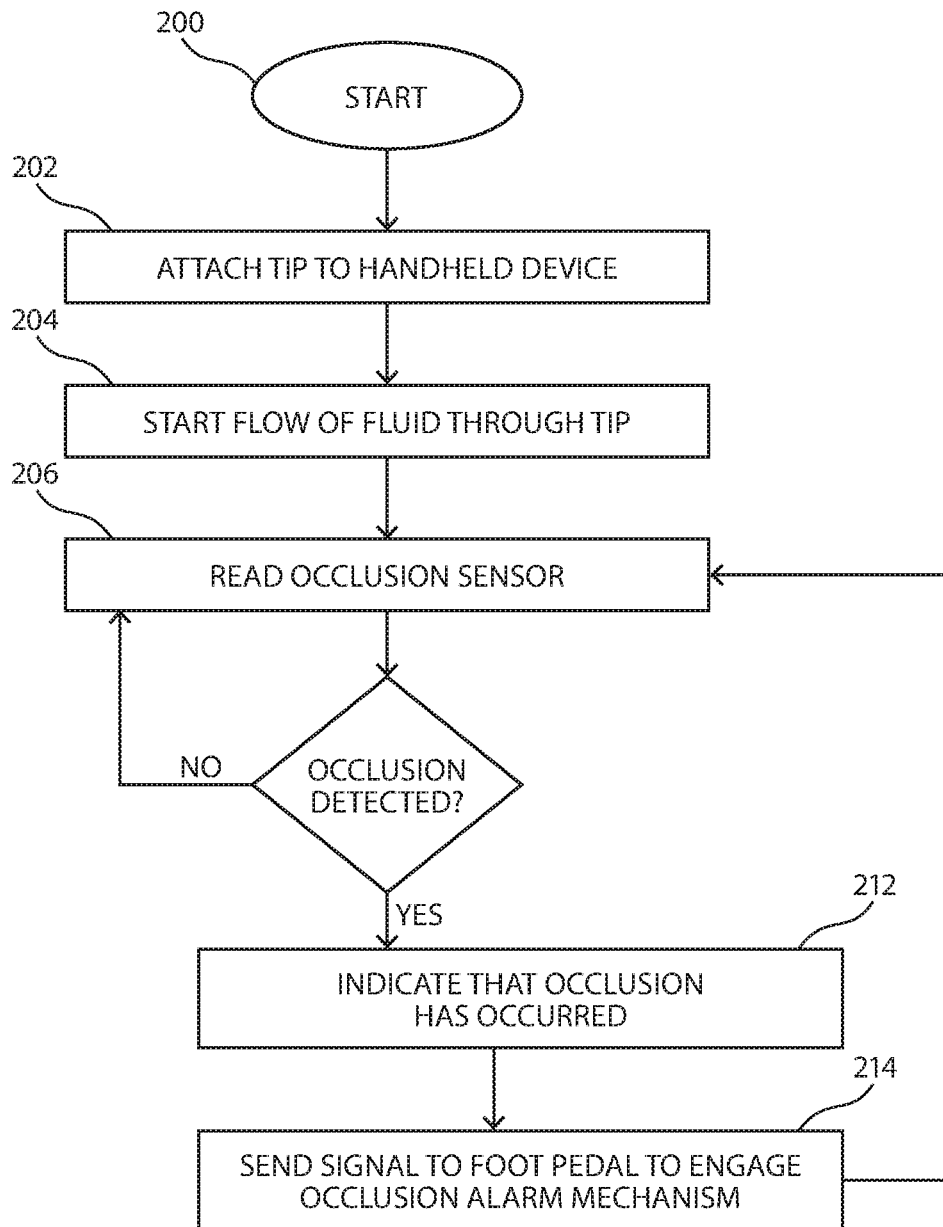

As illustrated in FIG. 7, the process of indicating an occlusion is configured to occur during the surgical procedure. In illustrative embodiments, the surgical procedure is started at step 200, and a tip 24 is attached to the handpiece 20 at step 202. Fluid begins to flow through the tip 24 at step 204 in order for the surgeon to irrigate and aspirate the eye of the patient. During this procedure, an occlusion sensor is configured to determine if an occlusion has occurred in the tip 24, as shown in step 206. If an occlusion has not occurred, the system will continue to perform as normal and no indicator or warning will be conveyed to the operator, as shown in steps 208 and 210. The system may be configured to continuously determine if an occlusion has occurred, for example as shown in the transition from step 210 to step 206, at predetermined time intervals. In an another embodiment, the system may be configured to detect an occlusion upon an occurrence of an event, e.g. detection of a decrease in flow rate and/or increase in vacuum rate and/or increase in vacuum above a preprogrammed or set threshold. If an occlusion has been detected, the system may indicate that occlusion has occurred in step 212, and thereafter send a signal to the foot pedal 50 to engage the occlusion alarm 80 in step 214. If the occlusion alarm 80 alerts the operator of an occlusion, the operator may then adjust the procedure accordingly to avoid detrimental effects of the occlusion. The system may be configured to continuously determine if an occlusion still exists, for example as shown in the transition from step 214 to step 206, at predetermined time intervals. If the system detects that no occlusion exists anymore, than the system will stop sending a signal to the foot pedal 50 to engage the occlusion alarm 80, as illustrated in step 210, the occlusion alarm 80 may stop indicating an occlusion has occurred. As further illustrated in FIG. 8, if no occlusion is detected, the system may continue to continuously determine if an occlusion exists by, for example, reading occlusion sensor 206.

In illustrative embodiments, the control module 60 is configured to monitor and control various components of the system 100, including the handpiece 20 and whether the tip 24 of the handpiece 20 is occluded. The control module 60 may be in a variety of forms as known in the art. In illustrative embodiments, the control module 60 may include a microprocessor computer 110, a keyboard 112, and a display or screen 114, as illustrated in FIG. 1. The microprocessor computer 110 may be operably connected to and control various other components of the system, including the functionality and operation of the handpiece 20 and the vibration mechanism 78 or feedback mechanism 76 of the foot pedal 50. The keyboard 112 and display 114 permit a user to interact with and control the system components as well. As may be appreciated by those skilled in the arts, and virtual keyboard and/or touchscreen, for example, may be used to provide the same functionality of keyboard 122 and display 114. In illustrative embodiments, the control module 60 may also include a pulsed ultrasonic power source (not shown) that can be controlled by the computer 110 in accordance with known methods or algorithms in the art.

In an embodiment of the present invention, a method of detecting an ocular occlusion may comprise the generation of at least one signal from the occlusion sensor 206 when, for example, the tip 24 of the handpiece 20 is occluded. The signal generated may be of a length or strength relative to the occlusion encountered. By way of example, an occlusion may be discrete but may be large enough to create a large drop in pressure in the handpiece 20 for which a relatively high frequency signal may be read by the control module 60 for the actuation of an alert indicative of such an occlusion. Similarly, a plurality of occlusions may not result in a relatively large pressure drop but may, for example, propagate a pressure drop over a larger period of time for which a signal may be produced over substantially the same period of time to allow for an alert commensurate with the length of time the pressure in the handpiece 20 deviates or varies from the desired or predetermined pressure in the handpiece 20.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Any options available for a particular medical device system may be employed with the present invention. For example, with a phacoemulsification system the available settings may include, but are not limited to, irrigation, aspiration, vacuum level, flow rate, pump type (flow based and/or vacuum based), pump speed, ultrasonic power (type and duration, e.g. burst, pulse, duty cycle, etc.), irrigation source height adjustment, linear control of settings, proportional control of settings, panel control of settings, and type (or "shape") of response. As noted, control of the functionality or settings of the system may be performed by use of a foot pedal. Conversely, the system may notify a user of a system or environmental characteristic (such as an occlusion) by providing tactile feedback to a user via the foot pedal.

The tactile notification in a foot pedal provides feedback to the user should the pre-selected or automatic settings or criteria of the system need adjustment in light of an occlusion. Such adjustment may be necessary to ensure optimal use of the desired settings of the system and the desired outcome of the surgery. In alternative embodiments, the foot pedal can then also permit the user to change or modify those settings accordingly, for instance, by depressing a switch or the treadle on the foot pedal.

The term "phacoemulsification" refers to a method of lens and cataract extraction from an eye. The procedure includes an ultrasonically vibrated needle which is inserted through a very small incision in the cornea in order to provide energy for emulsifying or breaking up of the lens and cataract which then can be aspirated and removed through the incision.

The term "vitrectomy surgery" refers to a method employed during cataract surgery when the posterior capsular bag has been broken and in the treatment of retinal detachments resulting from tears or holes in the retina. In cataract surgery, the same incision used for the phacoemulsification handpiece is used for inserting the vitrector to remove the vitreous gel. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion/aspiration port(s), but these devices may be combined into one single tool as well.

The term "screen," "display," or "display screen" as used herein shall mean a graphical user interface (GUI), a screen, a monitor, touch screen, or any other device known in the art for displaying a visual picture, words, or representation.

The previous description is provided to enable any person skilled in the art to make or use the disclosed embodiments. Various modifications to these embodiments will be readily apparent to those skilled in the art, and the generic principles defined herein may be applied to other embodiments without departing from the spirit or scope of the invention. Thus, the present disclosure is not intended to be limited to the embodiments shown herein but is to be accorded the widest scope consistent with the principles and novel features disclosed herein.

What is claimed is:

1. A process of indicating that an occlusion has occurred in an ocular surgical apparatus, the process comprising:
   detecting by a sensor of the ocular surgical apparatus, the occlusion;
   generating, by a control module of the ocular surgical apparatus, a notification signal in response to the detecting of the occlusion;
   sending by the control module, the notification signal to a foot pedal of the ocular surgical apparatus, the foot pedal comprising a treadle and a body housing, the treadle being rotatably coupled to the body housing; and
   generating, by a mechanism of the foot pedal, a tactile indicator in the foot pedal when the foot pedal receives the notification signal.

2. The process of claim 1, wherein the tactile indicator is a vibration.

3. The process of claim 2, wherein the mechanism is a vibration mechanism comprising a motor and an off-center weight.

4. The process of claim 1, wherein the tactile indicator is a forced feedback.

5. The process of claim 1, wherein the foot peddle comprises a base.

6. The process of claim 5, wherein the mechanism is coupled to the base of the foot pedal and configured to remain stationary when the treadle is compressed.

7. The process of claim 1, wherein the tactile indicator provides feedback to a user with respect to whether settings or criteria of the ocular surgical apparatus needs adjustment in light of the occlusion.

8. The process of claim 1, wherein the mechanism is coupled to a surface of the treadle.

9. The process of claim 8, wherein the surface of the treadle is a bottom surface.

10. The process of claim 8, wherein the mechanism is configured to rotate with the treadle about a pivot point of the foot pedal when the treadle is pressed.

11. The process of claim 1, wherein the mechanism is configured in a heel portion of the foot pedal.

12. The process of claim 1, wherein the mechanism comprises a motor and a rotating vane wheel with one or more projections.

13. The process of claim 12, wherein the rotating vane wheel is configured to be rotated by the motor about a rotation axis to cause the one or more projections to engage with or hit against a surface of the treadle.

\* \* \* \* \*